(12) United States Patent
Lim et al.

(10) Patent No.: US 6,200,353 B1
(45) Date of Patent: Mar. 13, 2001

(54) COUPLER FOR USE IN OXIDATIVE HAIR DYEING

(75) Inventors: Mu-Ill Lim, Trumbull; Linas R. Stasaitis, Fairfield; Yuh-Guo Pan, Stamford, all of CT (US)

(73) Assignee: Bristol Myers Squibb Company, New York, NY (US)

( * ) Notice: Subject to any disclaimer, the term of this patent is extended or adjusted under 35 U.S.C. 154(b) by 0 days.

(21) Appl. No.: 09/495,582

(22) Filed: Feb. 1, 2000

(51) Int. Cl.$^7$ .................. A61K 7/13; C07D 207/30; C07D 307/34; C07D 333/04
(52) U.S. Cl. .................. 8/409; 8/408; 8/412; 8/421; 8/423; 8/574; 8/575; 8/577; 548/561; 548/562; 549/74; 549/75; 549/80; 549/81; 549/492; 549/495
(58) Field of Search .................. 8/408, 409, 410, 8/412, 421, 423, 574, 575, 577; 548/561, 562; 549/74, 75, 80, 81, 491, 492, 495

(56) References Cited

U.S. PATENT DOCUMENTS

| | | | |
|---|---|---|---|
| 2,624,743 | * | 1/1953 | Kyrides .................. 549/74 |
| 4,065,255 | | 12/1997 | Andrillon .................. 8/406 |

FOREIGN PATENT DOCUMENTS

| | | |
|---|---|---|
| 634 165 | 7/1994 | (FR) . |
| 0 667 143 | 11/1994 | (FR) . |

* cited by examiner

*Primary Examiner*—Caroline D. Liott
(74) *Attorney, Agent, or Firm*—Carmella A. Ogorman

(57) ABSTRACT

Couplers for hair coloring compositions for oxidative dyeing of hair are compounds of the formula at least one coupler comprising a compound of the formula:

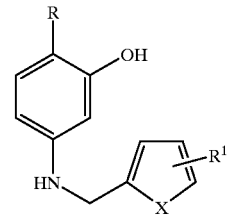

wherein R is selected from the group consisting of $C_1$ to $C_2$ alkyl and hydroxyethyl, $R^1$ is selected from the group consisting of hydrogen, chlorine, bromine, $C_1$ to $C_3$ alkyl, $C_1$ to $C_3$ alkoxy, $C_1$ to $C_3$ hydroxyalkyl and $C_1$ to $C_3$ hydroxyalkoxy, and X is O, S or NH.

17 Claims, No Drawings

COUPLER FOR USE IN OXIDATIVE HAIR DYEING

FIELD OF THE INVENTION

This invention relates to novel couplers for use in hair coloring compositions comprising one or more oxidative hair coloring agents in combination with one or more oxidizing agents. The invention also relates to hair coloring compositions of these novel couplers and to coloring or dyeing of hair using compositions containing these couplers.

BACKGROUND OF THE INVENTION

Coloration of hair is a procedure practiced from antiquity employing a variety of means. In modern times, the most extensively used method employed to color hair is to color hair by an oxidative dyeing process employing hair coloring systems utilizing one or more oxidative hair coloring agents in combination with one or more oxidizing agents.

Most commonly a peroxy oxidizing agent is used in combination with one or more oxidative hair coloring agents, generally small molecules capable of diffusing into hair and comprising one or more primary intermediates and one or more couplers. In this procedure, a peroxide material, such as hydrogen peroxide, is employed to activate the small molecules of primary intermediates so that they react with couplers to form larger sized complexes in the hair shaft to color the hair in a variety of shades and colors.

A wide variety of primary intermediates and couplers have been employed in such oxidative hair coloring systems and compositions. Among the primary intermediates employed there may be mentioned p-phenylenediamine, p-toluenediamine, p-aminophenol, 4-amino-3-methylphenol, and as couplers there may be mentioned resorcinol, 2-methylresorcinol, 3-aminophenol, and 5-amino-2-methylphenol. A majority of the shades have been produced with dyes based on p-phenylenediamine.

For providing an orange coloration to hair 2-methyl-5-aminophenol has been extensively used in combination with p-aminophenol as a primary intermediate. However, the resulting orange color on hair undergoes significant changes on exposure to light or shampooing. U.S. Pat. No. 4,065,255 and EP patent publications EP 634165 A1 and EP 667143 A1 suggest the use of 2-methyl-5-N-hydroxyethylaminophenol, 2-methyl-5-alkylaminophenol and 2-methyl-5-aminophenol as couplers. Therefore, there is a need for new orange couplers for use in oxidative hair dyeing compositions and systems.

BRIEF SUMMARY OF THE INVENTION

This invention provides novel orange couplers of the formula (1):

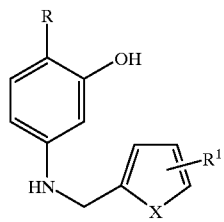

(1)

wherein R is selected from $C_1$ to $C_2$ alkyl and hydroxyethyl, $R^1$ is hydrogen, chlorine, bromine, $C_1$ to $C_3$ alkyl, $C_1$ to $C_3$ alkoxy, $C_1$ to $C_3$ hydroxyalkyl and $C_1$ to $C_3$ hydroxyalkoxy, and X is O, S or NH. These novel orange couplers are used to provide an orange coloration to hair in which there is good dye uptake by the hair and provides shades or colors which are stable over a relatively long period of time. The novel couplers provide for dyeing of hair that provides color or shades that possess good wash fastness and do not undergo the significant changes on exposure to light or shampooing as experienced with 2-methyl-5-aminophenol.

DETAILED DESCRIPTION OF THE INVENTION

Preferred coupler compounds of this invention are those of formula (1):

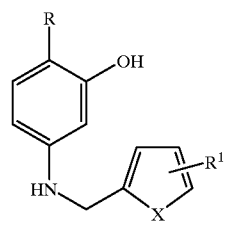

(1)

wherein R is a methyl group, R1 is a hydrogen atom and X is O, S or NH, most preferably NH.

Especially preferred couplers of this invention are the following compounds:

Compound A: 2-methyl-5-[(1H-pyrrol-2-yl-methyl)-amino]phenol,
Compound B: 2-methyl-5-(furan-2-yl-methylamino)phenol, and
Compound C: 2-methyl-5-(thiophen-2-yl-methylamino)phenol.

The novel coupler compounds of formula (1) of this invention are readily prepared by a reaction of an aminophenol of formula (2) with an appropriate carboxaldehyde of formula (3) in the presence of a suitable reducing agent, such as sodium borohydride, according to the following reaction sequence:

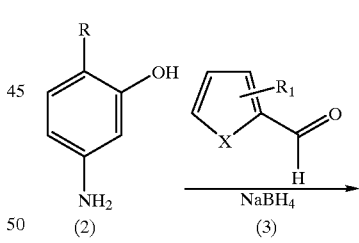

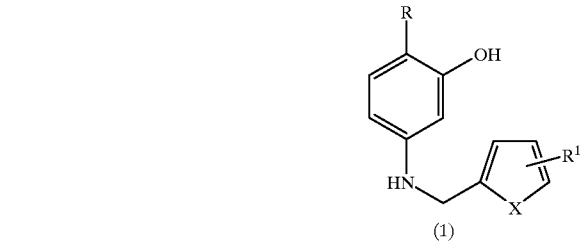

(1)

wherein R, $R^1$ and X are as defined hereinbefore and R is preferably a methyl group, $R^1$ a hydrogen atom and X is O, S or NH.

Compounds A, B and C were prepared in the following Synthesis Examples 1 to 3 according to the aforedescribed synthesis method.

SYNTHESIS EXAMPLE 1
Preparation of Compound A:

To a stirred solution of 5-amino-2-methylphenol (9.84 g, 80 mmole) in methanol (100 mL) at 4° C. was added pyrrole-2-carboxaldehyde (11.41 g, 120 mmole) and sodium acetate (13.13 g, 160 mmole). The reaction mixture was stirred for 15 minutes and sodium borohydride (3.78 g, 100 mmole) was added portionwise over 1 hour at 4° C. After the addition was complete, the reaction was allowed to stir for an additional 3 hours. The reaction mixture was poured onto crushed ice slurry (200 g) and the resulting precipitate was collected and washed with cold water three times and air-dried to afford 2-methyl-5-[(1H-pyrrol-2-yl-methyl)amino]phenol (6.62 g, 41% yield): mp 115.4–116.8° C.; $^1$HNMR (400 MHz, DMSO-$d_6$) δ 1.94 (s, 3H), 4.03 (d, 2H, J=5.6 Hz), 5.37 (t, 1H, J=5.6 Hz), 5.90 (m, 2H), 6.01 (dd, 1H, J=2.2, 8.0 Hz), 6.12 (d, 1H J=2.1 Hz), 6.61 (m, 1H), 6.70 (d, 1H, J=8.1 Hz), 8.77 (s, 1H), 10.64 (s, 1H); MS m/z 202 ($M^+$).

SYNTHESIS EXAMPLE 2
Preparation of Compound B:

To a stirred solution of 5-amino-2-methylphenol (12.30 g, 100 mmole) in methanol (100 mL) at 4° C. was added 2-furaldehyde (14.41 g, 150 mmole) and sodium acetate (16.41 g, 200 mmole). The reaction mixture was stirred for 15 minutes and sodium borohydride (4.73 g, 125 mmole) was added portionwise over 1 hour at 4° C. After the addition was complete, the reaction was allowed to stir for an additional 1.5 hours. The reaction mixture was poured onto crushed ice slurry (200 g) and the resulting precipitate was collected, washed with cold water three times and air-dried to afford 2-methyl-5-(furan-2-yl-methylamino)phenol (16.86 g, 83% yield): mp 126.8–128.5° C.; $^1$HNMR (400 MHz, DMSO-$d_6$) δ 1.94 (s, 3H), 4.12 (d, 2H, J=6.1 Hz), 5.71 (t, 1H, J=6.1 Hz), 6.00 (dd, 1H, J=2.3, 8.0 Hz), 6.11 (d, 1H, J=2.2 Hz), 6.22 (d, 1H, J=3.0 Hz 6.36 (m, 1H), 6.70 (d, 1H, J=8.1 Hz), 7.54 (t, 1H, J=0.8 Hz), 8.79 (s, 1H); MS m/z203 ($M^+$).

SYNTHESIS EXAMPLE 3
Preparation of Compound C:

To a solution of 5-amino-2-methylphenol (12.30 g, 100 mmole) in methanol (100 mL) at 4° C. was added 2-thiophenecarboxaldehyde (16.82 g, 150 mmole) and sodium acetate (16.41 g, 200 mmole). The reaction mixture was stirred for 15 minutes and sodium borohydride (4.73 g, 125 mmole) was added portionwise over 1 hour at 4° C. After the addition was complete, the reaction was allowed to stir for an additional 1.5 hours. The reaction mixture was poured onto crushed ice slurry (200 g) and the resulting precipitate was collected, washed with cold water three times and air-dried to afford 2-methyl-5-(thiophen-2-yl-methylamino)phenol (7.12 g, 32% yield): mp 30.8–132.6° C.; $^1$HNMR (400 MHz, DMSO-$d_6$) δ 1.94 (s, 3H), 4.34 (d, 2H, J=6.0 Hz) 5.91 (t, 1H, J=6.1 Hz), 6.00 (dd, 1H, J=2.3, 8.0 Hz), 6.11 (d, 1H, J=2.2 Hz), 6.70 (d, 1H, J=8.1 Hz), 6.95 (dd, 1H, J=3.5, 5.0 Hz), 7.00 (dd, 1H, J=0.8, 3.4 Hz), 7.34 (dd, 1H, J=1.0, 5.0 Hz), 8.79 (s, 1 H); MS m/z 219 ($M^+$).

Hair coloring compositions of this invention can contain the novel couplers of this invention as the sole coupler or can also contain other couplers in combination with primary intermediates.

Compound A couples with p-aminophenol and p-phenylenediamine to color piedmont hair bright orange and red-violet, respectively. Compound B's dye uptake is not as strong as that of Compound A and provides color of less brightness than Compound A. Compound C provides an even duller color to piedmont hair.

For hair coloring compositions of this invention, there may be used one or more suitable primary intermediates in combination with the novel couplers of this invention. Suitable primary intermediates include, for example, p-phenylenediamine derivatives such as: 2-methyl-p-phenylenediamine, p-phenylenediamine, 2-chloro-p-phenylenediamine, N-phenyl-p-phenylenediamine, N-(2-methoxyethyl)-p-phenylenediamine, N, N-bis(2-hydroxyethyl)-p-phenylenediamine, 2-hydroxymethyl-p-phenylenediamine, 2-(2-hydroxyethyl)-p-phenylenediamine, 4,4'diamino-diphenylamine, 2,6-dimethyl-p-phenylenediamine, 2-isopropyl-p-phenylenediamine, N-(2-hydroxypropyl)-p-phenylenediamine, 2-propyl-p-phenylenediamine, 1,3-bis[(N-hydroxyethyl)-N-(4-aminophenyl)amino]-2-propanol, 2-methyl-4-dimethylamino-aniline, 2-methoxy-p-phenylenediamine, 2,3-dimethyl-p-phenylenediamine, 2-(1-hydroxyethyl)-p-phenylenediamine, 2-(1,2-dihydroxyethyl)-p-phenylenediamine and 2-thiophen-2-yl-benzene-1,4-diamine, p-aminophenol derivatives such as: p-aminophenol, p-methylaminophenol, 3-methyl-4-aminophenol, 2-hydroxymethyl-4-aminophenol, 2-methyl-4-aminophenol, 2-(2'-hydroxyethylaminomethyl)-4-aminophenol, 2-methoxymethyl-4-aminophenol, 5-aminosalicylic acid, 1-(5-amino-2-hydroxyphenyl)-ethane-1,2-diol, o-aminophenol derivatives such as: o-aminophenol, 2,4-diaminophenol, 5-methyl-2-aminophenol, 6-methyl-2-aminophenol, 2-ethylamino-p-cresol and 2-amino-5-acetaminophenol, and 4-methyl-2-aminophenol, heterocyclic derivatives such as: 2,4,5,6-tetraaminopyrimidine, 4,5-diamino-1-methylpyrazole, 2-dimethylamino-5-aminopyridine, 1-(2-hydroxyethyl)-4,5-diaminopyrazole, 4-hydroxy-2,5,6-triaminopyrimidine, 2-(2-hydroxyethylamino)-6-methoxy-3-aminopyridine and 3-amino-2-methylamino-6-methoxypyridine.

The primary intermediates can be employed in the form of a free base or in the form of an acid additive salt thereof, such as, for example, as a hydrochloride, a hydrobromide, a sulfate or the like.

Suitable couplers include, for example, phenols, resorcinol and naphthol derivatives such as: 1,7-dihydroxynaphthalene, resorcinol, 4-chlororesorcinol, 1-naphthol, 2-methyl-1-naphthol, 1-acetoxy-2-methylnaphthalene, 1,5-dihydroxynaphthalene, 2,7-dihydroxynaphthalene, hydroquinone, 2-methylresorcinol, 1-hydroxy-6-aminonaphthalene-3-sulfonic acid, 2-isopropyl-5-methylphenol, 1,5-dihydroxy-1,2,3,4-tetrahydronaphthalene, 2-chlororesorcinol, 2,3-dihydroxy-1,4-naphthoquinone and 1-naphthol-4-sulfonic acid, 1,2,3-trihydroxybenzene, m-phenylenediamines such as: m-phenylenediamine, 2,4-diamino-phenoxyethanol, N,N-bis(2-hydroxyethyl)-m-phenylenediamine, 2,6-diaminotoluene, 2-N,N-bis (hydroxyethyl)-2,4-diaminophenetole, 1,3-bis(2,4-diaminophenoxy)propane, 1-hydroxyethyl-2,4-diaminobenzene, 2-amino-4-(2-hydroxyethylamino) anisole, 4-(2-aminoethoxy)-1,3-diaminobenzene, 2,4-diaminophenoxyacetic acid, 4,6-bis(2-hydroxyethoxy)-m-phenylenediamine, 2,4-diamino-5-methylphenetole, 2,4-diamino-5-hydroxyethoxy-toluene, 2,4-dimethoxy-1,3-diaminobenzene and 2,6- bis(2-hydroxyethylamino)-toluene, 3-(2,4-diaminophenoxy)-1-propanol, m-aminophenols such as: m-aminophenol, 2-hydroxy-4-(carbamoyl-methylamino) toluene, m-carbamoylmethylaminophenol, 6-hydroxybenzomorpholine, 2-hydroxy-4-aminotoluene, 2-hydroxy-4-(2-hydroxyethylamino) toluene, 4,6-dichloro-m-amino-phenol, 2-methyl-m-aminophenol, 2-chloro-6-methyl-m-aminophenol, 2-(2-hydroxyethoxy)-5-aminophenol, 2-chloro-5-trifluoroethylaminophenol, 4-chloro-6-methyl-m-aminophenol, N-cyclopentyl-3-aminophenol, N-hydroxyethyl-4-methoxy-6-methyl-m-aminophenol and 5-amino-4-methoxy-2-methylphenol, and heterocyclic derivatives such as: 1-phenyl-3-methyl-5-pyrazolone, 6-methoxy-8-aminoquinoline, 2,6-dihydroxy-4-methylpyridine, 5-hydroxy-1,4-benzodioxane, 3,4-methylenedioxyphenol, 4-(2-hydroxyethylamino)-1,2-methylenedioxybenzene, 2,6-dihydroxy-3,4-dimethylpyridine, 5-chloro-2,3-dihydroxypyridine, 3,5-diamino-2,6-dimethoxypyridine, 3,4-methylene-dioxyaniline, 2,6-bis (2-hydroxyethoxy)-3,5-diaminopyridine, 4-hydroxyindole, 3-amino-5-hydroxy-2,6-dimethoxypyridine, 5,6-dihydroxyindole, 7-hydroxyindole, 5-hydroxyindole, 2-bromo-4,5-methylenedioxyphenol, 6-hydroxyindole, 2-amino-3-hydroxypyridine, 2,6-diaminopyridine, 5-(3,5-diamino-2-pyridyloxy)-1,3-dihydroxypentane, 3-(3,5-diamino-2-pyridyloxy)-2-hydroxypropanol and isatin.

Preferred primary intermediates include:

p-phenylenediamine derivatives such as: 2-methyl-p-phenylenediamine, p-phenylenediamine, N-(2-methoxyethyl)-p-phenylenediamine, N,N-bis(2-hydroxyethyl)-p-phenylenediamine, 2-(1-hydroxyethyl)-p-phenylenediamine 2-(2-hydroxyethyl)-p-phenylenediamine, and 2-(1,2-dihydroxyethyl)-p-phenylenediamine, p-aminophenol derivatives such as: p-aminophenol, p-methylaminophenol, 3-methyl-4-aminophenol, 2-methoxymethyl-4-aminophenol, 1-(5-amino-2-hydroxyphenyl)-ethane-1,2-diol, o-aminophenol derivatives such as: o-aminophenol, 2-ethylamino-p-cresol, 5-methyl-2-aminophenol, 6-methyl-2-aminophenol and 2-amino-5-acetaminophenol, 4-methyl-2-aminophenol, and heterocyclic derivatives such as: 2,4,5,6-tetraaminopyrimidine 4,5-diamino-1-methylpyrazole, 1-(2-hydroxyethyl)-4,5-diaminopyrazole, and 2-dimethylamino-5-aminopyridine.

Preferred couplers include:

phenols, resorcinol and naphthol derivatives such as: 2-methyl-1-naphthol, 1-acetoxy-2-methyinaphthalene, 1,7-dihydroxynaphthalene, resorcinol, 4-chlororesorcinol, 1-naphthol, 1,5-dihydroxynaphthalene, 2,7-dihydroxynaphthalene, hydroquinone, 2-methylresorcinol and 2-isopropyl-5-methylphenol, m-phenylenediamines such as: m-phenylenediamine, 2,4-diamino-phenoxyethanol, 1,3-bis(2,4-diaminophenoxy)propane, 2-amino-4-(2-hydroxyethylamino)anisole and 4,6-bis(2-hydroxyethoxy)-m-phenylenediamine, 3-(2,4-diaminophenoxy)-1-propanol, m-aminophenols such as: m-aminophenol, 6-hydroxybenzomorpholine, 2-hydroxy-4-aminotoluene, 2-hydroxy-4-(2-hydroxyethylamino) toluene and 2-methyl-m-aminophenol, and heterocyclic derivatives such as: 1-phenyl-3-methyl-5-pyrazolone, 3,4-methylenedioxyphenol, 3,4-methylenedioxyaniline, 4-hydroxyindole, 5,6-dihydroxyindole, 7-hydroxyindole, 5-hydroxyindole, 6-hydroxyindole, isatin, 2,6-diaminopyridine and 2-amino-3-hydroxypyridine.

Most preferred primary intermediates include:

p-phenylenediamine derivatives such as: 2-methyl-p-phenylenediamine, p-phenylenediamine, N,N-bis(2-hydroxyethyl)-p-phenylenediamine and 2-(1-hydroxyethyl)-p-phenylenediamine, 2-(2-hydroxyethyl)-p-phenylenediamine, p-aminophenol derivatives such as: p-aminophenol, p-methylaminophenol, 3-methyl-4-aminophenol and 1-(5-amino-2-hydroxyphenyl)-ethane-1,2-diol, o-amino derivatives such as: o-aminophenol, 2-ethylamino-p-cresol, 5-methyl-2-aminophenol, 6-methyl-2-aminophenol and 2-amino-5-acetaminophenol, heterocyclic derivatives such as: 2,4,5,6-tetraaminopyrimidine, 1-(2-hydroxyethyl)-4,5-diaminopyrazole.

Most preferred couplers include:

phenols, resorcinol and naphthol derivatives such as: 2-methyl-1-naphthol, 1-acetoxy-2-methylnaphthalene, resorcinol, 4-chlororesorcinol, 1-naphthol and 2-methylresorcinol, m-phenylenediamines such as: 2,4-diaminophenoxyethanol, 2-amino-4-(2-hydroxyethylamino)anisole and 4,6-bis(2-hydroxyethoxy)-m-phenylenediamine, and 3-(2,4-diaminophenoxy)-1-propanol, m-aminophenols such as: m-aminophenol, 6-hydroxybenzomorpholine, 2-hydroxy-4-aminotoluene, 2-hydroxy-4-(2-hydroxyethylamino) toluene and 2-methyl-m-aminophenol, and heterocyclic derivatives such as: 1-phenyl-3-methyl-5-pyrazolone, 2-amino-3-hydroxypyridine and 6-hydroxyindole.

The hair coloring compositions of this invention will contain the couplers of this invention, alone or in combination with other couplers, in an effective coloring amount, generally in an amount of from about 0.01 to about 2.5 weight percent. Other couplers, when present will be present in an amount up to about 2.5 weight percent. The primary intermediate(s) will generally be present in an amount of from about 0.01 to about 3.5 weight percent. The molar ratio of primary intermediate to coupler will generally range from about 5:1 to about 1:5 and be employed in any suitable carrier or vehicle, generally an aqueous or hydroalcoholic solution, preferably an aqueous solution. The carrier or vehicle will generally comprise up to about 40 weight percent.

The hair coloring compositions of this invention may contain one or more cationic, anionic or amphoteric surface active agents, perfumes, antioxidants, sequestering agents, thickening agents, alkalizing or acidifying agents, and other dyeing agents.

Any suitable peroxide providing agent can be employed in the coloring compositions of this invention, particularly hydrogen peroxide ($H_2O_2$) or precursors therefor.

In general, a first composition of primary intermediate(s) and coupler(s) is prepared and then, at the time of use, the oxidizing agents, such as $H_2O_2$, is admixed therewith until an essentially homogenous composition is obtained which is applied to the hair to be dyed and permitted to remain in contact with the hair for a dyeing effective amount of time, generally for a period of from about 2 to 45, preferably about 2 to 30, minutes, after which the hair is rinsed, shampooed and dried.

The following compositions shown in Table 1 were used for dyeing piedmont hair. The dyeing solution was mixed with 100 g of 20 volume hydrogen to peroxide. The resulting mixture is applied to the hair and permitted to remain in contact with hair for 30 minutes. This dyed hair is then shampooed and rinsed with water and dried. The results are shown in Tables 2, 3 and 4. Minolta spectrophotometer CM-3700d from Minolta Co. is used. Color space is CIEL *a*b* and illuminant is D65 daylight with 10° observer. The color space, L* indicates lightness and a* and b* are the chromaticity coordinates. +a* is the red direction, −a* direction is the green direction, +b* is the yellow direction and −b* is the blue direction

TABLE 1

Composition for the Dyeing Solution

| Ingredients | Weight (%) |
|---|---|
| Cocamidopropyl betaine | 17.00 |
| Monoethanolamine | 2.00 |
| Oleic Acid | 0.75 |
| Citric Acid | 0.10 |
| Ammonium hydroxide | 5.00 |
| Behentrimonium chloride | 0.50 |
| Sodium sultite | 0.10 |
| EDTA | 0.10 |
| Erythorbic acid | 0.40 |
| Ethoxydiglycol | 3.50 |
| C11–15 Pareth-9 (Tergitol 15-S-9) | 1.00 |
| C12–15 Pareth-3 (Neodol 25-3) | 0.50 |
| Isopropanol | 4.00 |
| Propylene glycol | 2.00 |
| p-aminophenol | 5 mmole |
| Coupler (of this invention or prior art) | 5 mmole |
| Water | qs to 100.00 |

TABLE 2

Coupling of p-aminophenol with Compounds A, B and C

| Coupler Compound | L* | a* | b* |
|---|---|---|---|
| A | 44.55 | 28.05 | 29.08 |
| B | 48.08 | 24.35 | 29.63 |
| C# | 56.93 | 20.09 | 27.51 |

Half of the concentration was used due to low solubility in dye base tested.

Surprisingly, dye-uptake of Compound A on piedmont hair when coupled with p-aminophenol is almost identical to that of the prior art compound 2-methyl-5-N-hydroxyethylaminophenol even though the size of Compound A is bigger than the prior art compound (Table 3). In addition, the Compound A is a two-ring system, while the prior art compound is a one-ring system. Compound B colors hair weaker (48.08 vs. 44.55) and less bright (a*:24.35 vs. 28.05) than Compound A (Table 2).

TABLE 3

Coupling of p-aminophenol with Compounds A, B and C

| Coupler Compound | L* | a* | b* |
|---|---|---|---|
| A | 44.55 | 28.05 | 29.08 |
| Prior Art++ | 46.44 | 28.22 | 29.78 |
| B | 48.08 | 24.35 | 29.63 |

++ 2-methyl-5-N-hydroxyethylaminophenol

Wash Fastness Test

Piedmont hair dyed with p-aminophenol and Compound A was immersed in 10% Herbal Essences™ shampoo and shaken for 6 hours at room temperature. The results are shown in Table 4. Wash fastness test has shown that overall color change represented by ΔE is 7.58.

TABLE 4

Wash Fastness Test of Dyes with p-aminophenol

| Coupler | Before Shampooing | | | After 6 hr Shampooing | | | |
|---|---|---|---|---|---|---|---|
|  | L* | a* | b* | L* | a* | b* | ΔE |
| Compound A | 47.24 | 25.58 | 27.78 | 45.16 | 18.88 | 24.91 | 7.58 |

$$\Delta E = \sqrt{(\Delta L^*)^2 + (\Delta a^*)^2 + (\Delta b^*)^2}$$

With the foregoing description of the invention, those skilled in the art will appreciate that modifications may be made to the invention without departing from the spirit thereof. Therefore, it is not intended that the scope of the invention be limited to the specific embodiments illustrated and described.

We claim:

1. A compound of the formula:

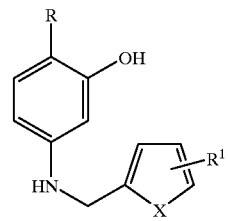

wherein R is selected from the group consisting of $C_1$ to $C_2$ alkyl and hydroxyethyl, $R^1$ is selected from the group consisting of hydrogen, chlorine, bromine, $C_1$ to $C_3$ alkyl, $C_1$ to $C_3$ alkoxy, $C_1$ to $C_3$ hydroxyalkyl and $C_1$ to $C_3$ hydroxyalkoxy, and X is O, S or NH.

2. A compound of claim 1 wherein R is methyl and $R^1$ is hydrogen.

3. A compound of claim 2 wherein X is O.

4. A compound of claim 2 wherein X is S.

5. A compound of claim 2 wherein X is NH.

6. A process for the preparation of a compound of claim 1 comprising reacting an aminophenol of the formula:

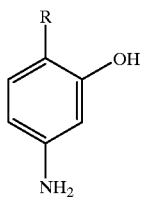

with a carboxaldehyde of the formula:

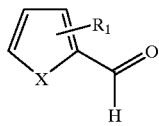

in the presence of a reducing agent, wherein R is selected from the group consisting of $C_1$ to $C_2$ alkyl and hydroxyethyl, $R^1$ is selected from the group consisting of hydrogen, chlorine, bromine, $C_1$ to $C_3$ alkyl, $C_1$ to $C_3$ alkoxy, $C_1$ to $C_3$ hydroxyalkyl and $C_1$ to $C_3$ hydroxyalkoxy, and X is O, ,S or NH.

7. A process according to claim 6 wherein R is methyl and $R^1$ is hydrogen.

8. A process according to claim 7 wherein X is O.

9. A process according to claim 6 wherein the reducing agent is selected from the group consisting of sodium borohydride and sodium triacetoxyborohydride.

10. In a hair coloring system comprising a composition containing one or more oxidative hair coloring agents and a composition containing one or more oxidizing agents, the improvement comprising the presence in the composition containing one or more oxidative hair coloring agents of a coupler comprising a compound of the formula:

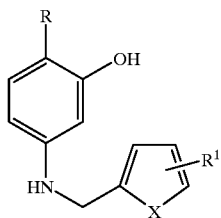

wherein R is selected from the group consisting of $C_1$ to $C_2$ alkyl and hydroxyethyl, $R^1$ is selected from the group consisting of hydrogen, chlorine, bromine, $C_1$ to $C_3$ alkyl, $C_1$ to $C_3$ alkoxy, $C_1$ to $C_3$ hydroxyalkyl and $C_1$ to $C_3$ hydroxyalkoxy, and X is O, S or NH.

11. A hair coloring system according to claim 10 wherein the composition comprising one or more oxidative hair coloring agents additionally comprises one or more primary intermediates selected from the group consisting of: 2-methyl-p-phenylenediamine, p-phenylenediamine, N,N-bis($_2$-hydroxyethyl)-p-phenylenediamine, 2-(1-hydroxyethyl)-p-phenylenediamine, 2-(2-hydroxyethyl)-p-phenylenediamine, p-aminophenol, p-methylaminophenol, 3-methyl-4-aminophenol, 1-(5-amino-2-hydroxyphenyl)-ethane-1,2-diol, o-aminophenol, 2-ethylamino-p-cresol, 5-methyl-2-aminophenol, 6-methyl-2-aminophenol, 2-amino-5-acetaminophenol, 2,4,5,6-tetraaminopyrimidine, and 1-($_2$-hydroxyethyl)-4,5-diaminopyrazole.

12. A hair coloring system according to claim 11 wherein the coupler compound is 2-methyl-5-[(1H-pyrrol-$_2$-yl-methyl)-amino]phenol.

13. In a system for coloring hair wherein at least one primary intermediate is reacted with at least one coupler in the presence of an oxidizing agent to produce an oxidative hair dye, the improvement comprising wherein the at least one coupler comprises a compound of the formula:

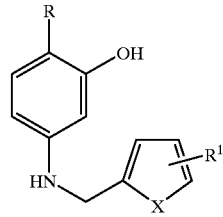

wherein R is selected from the group consisting of $C_1$ to $C_2$ alkyl and hydroxyethyl, Ris selected from the group consisting of hydrogen, chlorine, bromine, $C_1$ to $C_3$ alkyl, $C_1$ to $C_3$ alkoxy, $C_1$ to $C_3$ hydroxyalkyl and $C_1$ to $C_3$ hydroxyalkoxy, and X is O, S or NH.

14. A system for coloring hair according to claim 13 wherein the primary intermediate is selected from the group consisting of: 2-methyl-p-phenylenediamine, p-phenylenediamine, N,N-bis(2-hydroxyethyl)-p-phenylenediamine, 2-(1-hydroxyethyl)-p-phenylenediamine, 2-(2-hydroxyethyl)-p-phenylenediamine, p-aminophenol, p-methylaminophenol, 3-methyl-4-aminophenol, 1-(5-amino-2-hydroxyphenyl)-ethane-1,2-diol, o-aminophenol, 2-ethylamino-p-cresol, 5-methyl-2-aminophenol, 6-methyl-2-aminophenol, 2-amino-5-acetaminophenol, 2,4,5,6-tetraaminopyrimidine, and 1-(2-hydroxyethyl)-4,5-diaminopyrazole and mixtures thereof.

15. A system for coloring hair according to claim 14 wherein the coupler compound is 2-methyl-5-[(1h-pyrrol-2-yl-methyl)-amino]phenol.

16. A hair coloring composition for dyeing human hair comprising, in a suitable carrier or vehicle, a dyeing effective amount of:
(a) at least one primary intermediate,
(b) at least one coupler comprising a compound of the formula:

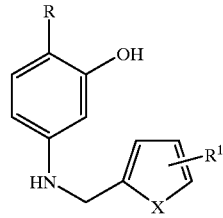

wherein R is selected from the group consisting of $C_1$ to $C_2$ alkyl and hydroxyethyl, $R^1$ is selected from the group consisting of hydrogen, chlorine, bromine, $C_1$ to $C_3$ alkyl, $C_1$ to $C_3$ alkoxy, $C_1$ to $C_3$ hydroxyalkyl and $C_1$ to $C_3$ hydroxyalkoxy, and X is O, S or NH, and
(c) at least one oxidizing agent.

17. A process for dyeing human hair comprising applying a dyeing effective amount of a hair coloring composition of claim 16 to the hair and permitting the composition to contact the hair for a dyeing effective period of time, and then rinsing, shampooing and drying the hair.

\* \* \* \* \*